United States Patent [19]

Folsom et al.

[11] 4,111,753

[45] Sep. 5, 1978

[54] CONTROLLED ATMOSPHERE APPARATUS AND METHOD OF TRANSFERRING SPECIMENS TO SAME

[75] Inventors: Max H. Folsom, Portland, Oreg.; Michael D. Dickman, Philadelphia, Pa.

[73] Assignee: National Appliance Company, Portland, Oreg.

[21] Appl. No.: 693,624

[22] Filed: Jun. 7, 1976

[51] Int. Cl.² ............................................. C12K 1/10
[52] U.S. Cl. ................................... 195/126; 195/127; 312/1
[58] Field of Search ................ 195/127, 103.5 R, 126, 195/104; 128/1, 1 B; 312/1

[56] References Cited

U.S. PATENT DOCUMENTS

| 2,786,740 | 3/1957 | Taylor et al. | 312/1 |
| 3,187,744 | 6/1965 | Dorsak et al. | 128/1 B |
| 3,775,256 | 11/1973 | Risinger | 195/127 X |
| 3,907,389 | 9/1975 | Cox et al. | 312/1 |

*Primary Examiner*—Alvin Tanenholtz
*Assistant Examiner*—Robert J. Warden
*Attorney, Agent, or Firm*—Klarquist, Sparkman, Campbell, Leigh, Hall & Whinston

[57] ABSTRACT

A controlled atmosphere apparatus comprising a rigid base and a transparent plastic hood is disclosed. The apparatus is suitable for use as an anaerobic incubator and is provided with a docking mechanism to receive a transport unit. A transport unit suitable for the transport of anaerobes and method of transporting anaerobes from remote locations to a controlled atmosphere apparatus are also disclosed.

19 Claims, 8 Drawing Figures

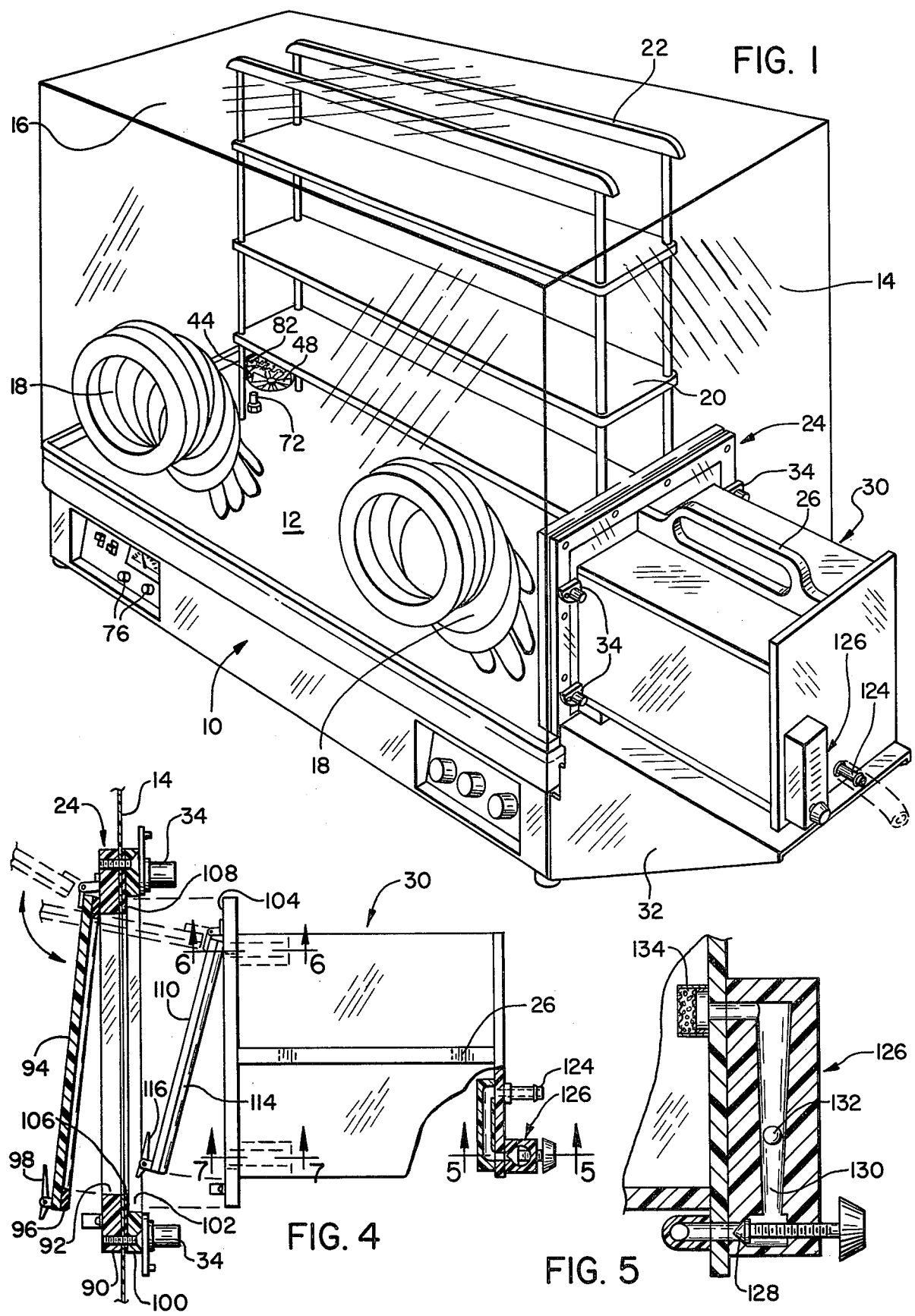

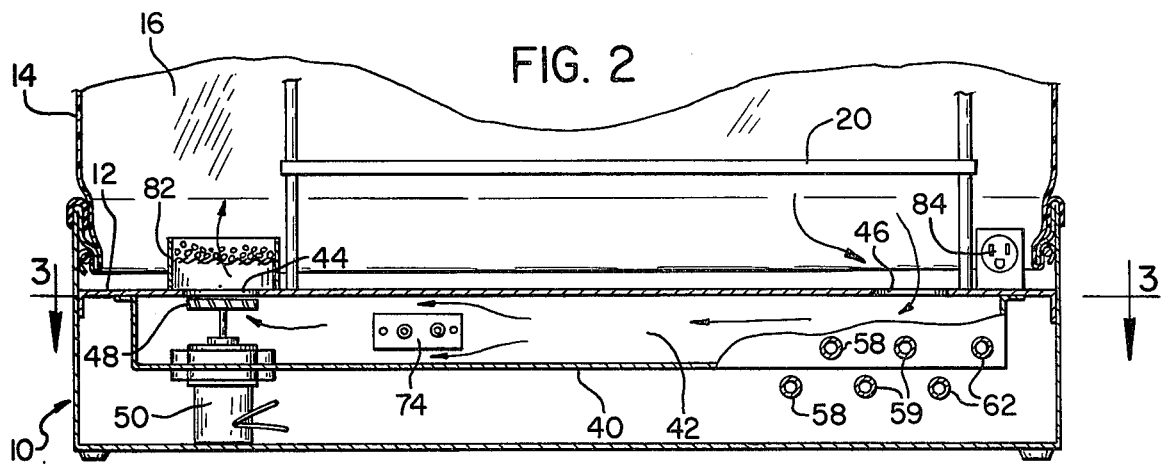
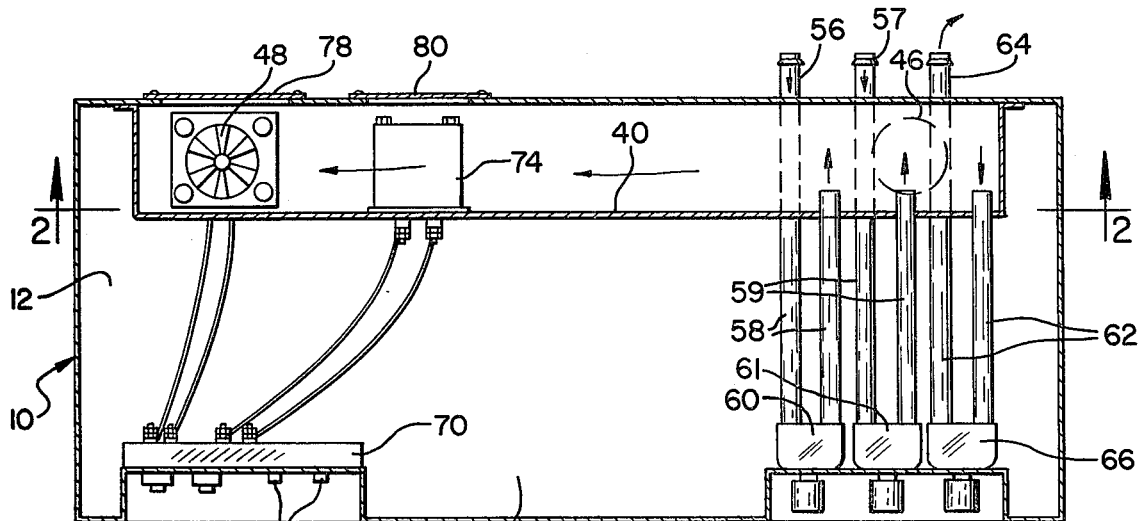
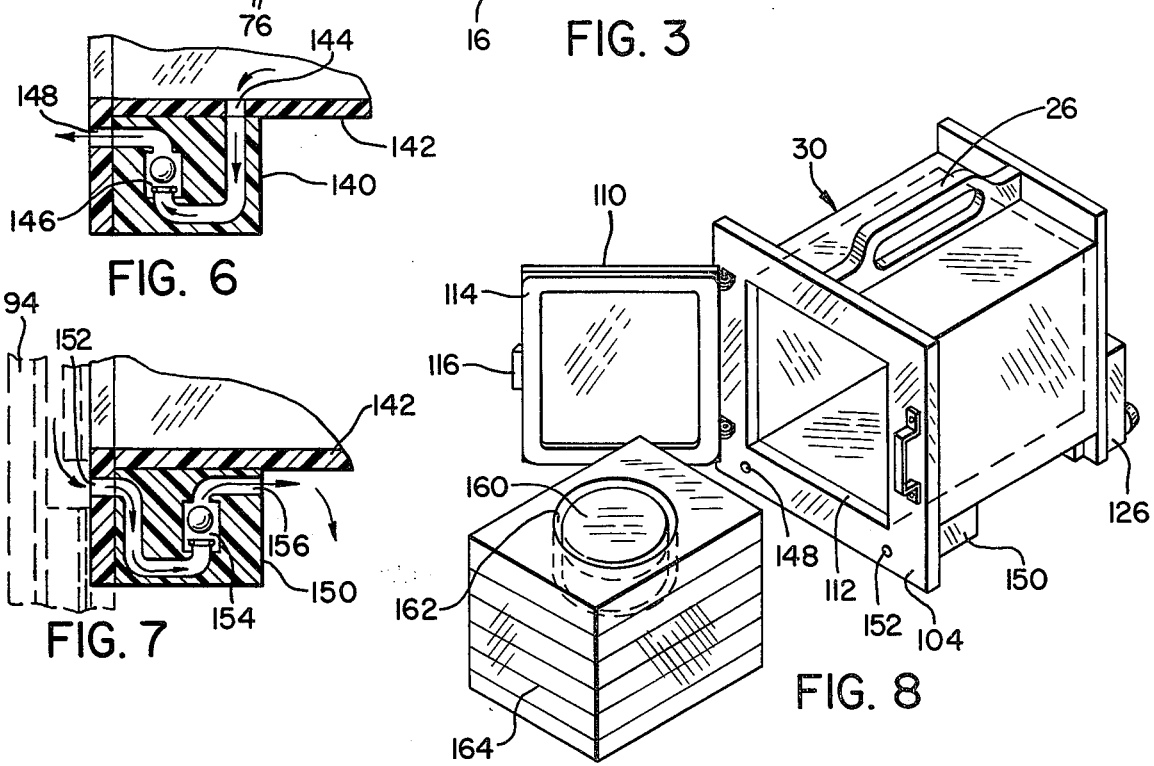

CONTROLLED ATMOSPHERE APPARATUS AND METHOD OF TRANSFERRING SPECIMENS TO SAME

BACKGROUND OF THE INVENTION

The present invention relates to an apparatus for maintaining a controlled environment. It is especially concerned with an incubation apparatus for the growth of anaerobes and with a process for transporting such organisms and the transfer of such organisms to and from such an apparatus.

The incubation of anaerobic micro-organisms is currently a difficult and sometimes dangerous task. Most anaerobes require an environment of approximately 37.5° C. temperature and an absence of oxygen for survival. Popular incubators presently in use are gove boxes which contain an atmosphere suitable for the growth of anaerobic organisms. Such incubators are of two basic types: (1) relatively simple plastic glove boxes consisting entirely of flexible plastic walls and containing a variety of equipment assembled for a particular experiment or procedure, and (2) complex metal chambers comprised or rigid materials except for the gloves. The simple devices typically require elaborate set up procedures before each use and are thus unsuitable for prolonged or routine use. The interior of such boxes are of necessity cluttered with equipment such as heaters, fans, connecting wires and the like which hinder maneuverability inside the chamber. The complex chambers are expensive and difficult to operate. They typically are provided with a few rigid viewing ports so that a microscope cannot be used unless it is specially constructed as a part of the chamber wall.

In all of the prior art devices it is difficult to transfer anaerobic specimens into or out of the incubation chamber. To perform this operation some of the more sophisticated prior devices have included an airlock, usually a vacuum airlock chamber, for transferring specimen containers directly from the outside atmosphere into the interior of an incubator. Because vacuum airlock chambers are evacuated of all gas during the transfer of samples, such airlocks have of necessity been constructed of heavy, high strength materials to prevent collapse during evacuation.

Anaerobic micro-organisms will die quickly in an aerobic atmosphere. For this reason airlock pass-throughs are only suitable if the specimen is collected at a location very near to the incubator itself or is transported to the incubator is specimen containers which are self-contained anaerobic units. In institutions such as hospitals where anaerobic specimens are collected at patients' bed sides and other locations remote from a central laboratory, use of anaerobic specimen containers is almost mandatory. Prior incubators have proved to be unsatisfactory in such institutions because currently available anaerobic specimen containers are difficult to operate and often ineffective in sustaining anaerobes during their transport to the incubator.

The vessels commonly used for the transport of anaerobic specimens comprise tanks containing a liquid culture medium. When such vessels are used, specimens must be prepared in a liquid medium and transferred into a tank. The tank is then transported to the incubator and passed through an airlock or its liquid contents are pumped into a storage tank inside the incubator. This arrangement is very inflexible and complicated. It requires extra process steps and equipment and limits the user to liquid culture medium. Special glassware for containing anaerobic cultures is available but is also difficult to use and frequently ineffective.

SUMMARY OF THE INVENTION

The present invention is an incubation apparatus and method of specimen handling suitable for the culture of anaerobes. The incubation apparatus includes an incubation chamber defined by a rigid base unit and a flexible plastic hood. Gas flow and temperature control components and a plenum for the recirculation of gases are all enclosed within the base unit, and thus the entire chamber is available for specimens. The temperature control components are of a plug-in type which can be easily replaced without affecting the atmosphere inside the chamber. The transparent, flexible, plastic hood allows specimens to be easily observed by the operator who can even manipulate the hood to look into the eyepiece of a microscope inside the chamber. The hood is supported by gas pressure inside the chamber and may be inflated or deflated by increasing or reducing the pressure. The apparatus includes a door mechanism and a transport unit designed to dock with the door mechanism. Specimens collected at remote locations are placed in the transport unit, and the transport unit continuously flushed with an anaerobic gas mixture at pressures above atmospheric to displace oxygen-bearing gases while the transport unit, with the culture of anaerobic specimens enclosed, is transported to the incubator. After the transport unit is docked with the incubator, specimens are transferred to the incubator without exposure to the surrounding atmosphere. The transport unit is simple, inexpensive and is constructed of lightweight materials. It can accommodate anaerobic specimens in any culture medium and in any type of laboratory glassware and can be reused immediately after specimens are transferred to the incubation chamber.

It is an object of this invention to provide an improved controlled atmosphere apparatus in which anaerobic microorganisms may be simply and safely cultured on a routine basis.

It is a further object to provide an improved controlled atmosphere apparatus wherein the environmental control equipment is incorporated into a base unit so that the entire interior of the airtight incubation chamber is uncluttered and can thus be devoted to specimen containers and the like.

Another object is to provide an improved controlled atmosphere apparatus with a docking means adapted to form an airlock with a transport unit so that solid specimens may be transferred from the transport unit to the incubator.

An additional object is to provide an improved airlock device which dispels oxygen-bearing gases by gas displacement and thus may be constructed of inexpensive, lightweight materials.

Another object of the invention is to provide an improved transport unit for use with a controlled environmental apparatus in which a flow of any desired gas moves continuously through the container during transport and which can accommodate anaerobic specimens in any type of glassware.

A further object is to provide an improved incubation apparatus in which a conventional light microscope may be used.

Another object is to provide an improved method of transporting micro-organisms from remote locations to a centrally located incubator without exposure to the outside atmosphere.

BRIEF DESCRIPTION OF THE DRAWINGS

In the drawings:

FIG. 1 is a perspective view of the controlled atmosphere apparatus according to the present invention with the transport unit in the docked position;

FIG. 2 is a vertical, sectional view of the base of the FIG. 1 apparatus;

FIG. 3 is a horizontal, sectional view taken along the lines 3—3 of FIG. 2;

FIG. 4 is a top view of the transport unit and door mechanism of the controlled atmosphere apparatus;

FIG. 5 is a vertical, sectional view taken along the lines 5—5 of FIG. 4;

FIG. 6 is a vertical, sectional view taken along the lines 6—6 of FIG. 4;

FIG. 7 is a vertical, sectional view taken along the lines 7—7 of FIG. 4; and

FIG. 8 is a perspective view showing the transport unit and filler block assemblies.

DESCRIPTION OF THE PREFERRED EMBODIMENT

The controlled atmosphere apparatus of the present invention is best described with reference to the drawings. In FIG. 1 the apparatus includes a base 10 of a rigid box-like construction having an upper wall 12 which serves as a floor for the chamber. Mounted on the base 10 is a hood 14 preferably made of a transparent, flexible material such as a clear vinyl plastic film and preferably comprising a plurality of walls joined by airtight seams. The hood 14 and base 10 are joined with an airtight seal so that together they define an airtight incubation chamber 16 to contain the usual glassware and other equipment for the culture of microbes. Elevated pressures are maintained inside the chamber so that the hood is inflated and thus self-supporting during normal operation. The top of the hood is also supported by support means 22 on which are mounted a plurality of shelves 20 to hold the specimen containers. Mounted on walls of the hood 14 are plastic gloves 18 or other similar remote handling means and a door frame 24 on which is hung a sealable chamber door means operable to admit specimens into the chamber. If the apparatus is being used for the incubation of anaerobes, the chamber door means is not normally opened directly to the atmosphere, but if it is accidentally opened, air will not pass into the chamber because anaerobic gases inside the chamber are maintained at a pressure greater than atmospheric and thus will flow out the door displacing the surrounding air. The outwardly facing side of the door frame 24 is adapted to receive a transport unit 30 which is preferably made of a lightweight, transport plastic material so that it can be easily moved and so that its contents may be visibly identified. Walls made of such a lightweight material define a transport chamber for containing specimens during transport to the chamber 16; and a handle 26 is provided for carrying the unit. When docked with the door frame 24, the transport unit 30 rests on a support 32 and is secured by clamps 34. In this position the door frame 24 and transport unit 30 together form an airlock means which includes an airlock compartment between the chamber door means and the transport unit so that the chamber door means may be opened without exposing the chamber to the surrounding atmosphere.

Located inside of the base 10, as shown in FIGS. 2 and 3, is a metal housing 40 welded to the bottom of the wall 12 to define a plenum 42. A chamber inlet means 44 is provided in the wall 12 for introducing a gaseous medium into the chamber from the plenum 42 and a chamber outlet means 46 is provied for exhausting the gaseous medium from the chamber into the plenum. The circulation of gaseous medium through the plenum 42 and the chamber 16 is accomplished by a blower 48 located inside the plenum 42 and driven by a motor 50 which blower draws gas through the plenum and into the chamber via the chamber inlet means 44.

Gas may be introduced into the plenum 42 from an external pressurized gas source (not shown) by connecting such a gas source to a gas connection 56 which communicates with an inlet tube 58 and then opening an inlet tube valve 60 which may be adjusted from the front of the apparatus. An additional gas connection 57, inlet tube 59, and tube valve 61 are optionally provided for admitting gas from a second source. Gas may be vented from the plenum through a gas outlet tube 62 and the outlet means 64 into the surrounding atmosphere by opening the outlet tube valve 66. Automatic, pressure-sensitive inlet and outlet valves are suitably provided to maintain a constant pressure inside the chamber.

The apparatus is provided with temperature control means for maintaining a constant temperature of the gas contained therein. Mounted on the wall 12 and wired to a temperature control module 70 on the inside of the base 10 is a temperature senser 72 (FIG. 1) for detecting the temperature inside the chamber. Responsive to the temperature senser 72 is a heating unit 74 inside the plenum 42 which warms gas circulating through the plenum before it enters the chamber 16 through the inlet 44. Controls 76 for adjusting the operating temperature are located on the front of the base along with indicator lights or a meter so that the operator can monitor the temperature inside the chamber.

The blower 48 and heating unit 74 are accessible through sealable doors 78, 80 on the back panel of the base 10. These components of the heat control system are preferably the plug-in type which may be quickly replaced without affecting the atmosphere in the chamber by plugging the chamber inlet and outlet means 44, 46 before opening the appropriate door 78, 80.

Inside the chamber 16, a catalyst tray 82 may be positioned over the chamber inlet 44 for a purpose described hereafter and a switched electric outlet 84 may conveniently be mounted on the wall 12 to provide electricity for a microscope or other electrical appliance to be used inside the chamber.

A more detailed view of the transport unit 30 and the docking mechanism appears in FIG. 4. Mounted on the inside of the hood 14 is an inner clamp frame 90 which defines an opening 92 of substantially the same or slightly larger dimensions than the inside dimension of the transport unit 30 so that the entire contents from the transport unit 30 can slide through the opening 92 and into the chamber 16. Hinged to the inner clamp frame 90 is a sealable chamber door 94 to close the opening 92. The door includes a gasket 96 to insure that an airtight seal is formed between the door 94 and the frame 90 and also includes a chamber door latch 98 operable from the inside of the chamber 16, to hold the door in a closed position.

Opposite the inner clamp frame 90 on the outside of the hood 14 is an outer clamp frame 100 defining an opening 102 which is larger than the opening 92 and slightly larger than a clamping surface 104 which comprises one wall of the transport unit 30. The inner and outer clamp frames 90, 100 are aligned such that a clamping shoulder 106 peripheral to the opening 92 is formed by the inner clamp frame 90. A gasket 108, located between the inner and outer clamping frames 90, 100 and extending to the periphery of the opening 92, forms a seal between the clamping surface 104 and the shoulder 106 when the transport unit is docked so that the door frame 24 and the transport unit 30 together form an airlock means.

Hinged on the clamping surface 104 is a transport door 110, smaller than the opening 92, to close an opening 112 (FIG. 8) in the clamping surface 104. The door is provided with a gasket 114 so that the door in the closed position is an airtight closure and a transport door latch 116 to hold the door in the closed position. The latch 116 is operable from the inside of the chamber 16 when the transport unit 30 is docked and the chamber door 94 is opened.

When the transport unit 30 is docked with the door frame 24 as shown in FIG. 1 and both of the doors are closed, the transport door 110 is opposed to the chamber door 94 and an airlock compartment is formed between the doors. Because an airtight seal is formed between the clamping surface 104 and the door frame 24, the doors may be opened and specimens transferred through the airlock compartment without exposure to the outside atmosphere. The doors are opened in two steps: First, the chamber door 94 is unlatched and swung into an open position inside the chamber. Second, the transport door 110 is unlatched and swung through the opening 92 into an open position inside the chamber 16 as indicated by broken lines in FIG. 4. With both door means in the open position, the transfer of specimens can commence.

The transport unit 30 also includes a gas circulation system which allows gas to pass through the unit at greater than atmospheric pressure when the transport door 110 is closed. Gas from a pressurized source (not shown) is introduced through a gas inlet 124 mounted on one wall of the transport unit 30 and delivered to a flow meter 126. The enlarged view of the flow meter (FIG. 5) shows a valve 128 provided as a flow regulator means for controlling the flow of the gaseous medium into the transport unit 30. Gas passing through the valve rises through a tube 130 and flows into the interior of the transport unit 30. The gas flow rate is indicated by the level to which a floating ball 132 rises in the tube 130. A catalyst container 134 may be provided at the top of the tube 130 for a purpose described below.

Gas is discharged from the transport unit through a valve block 140 (FIG. 6) located below the floor 142 of the transport unit 30. Gas flows through an inlet orifice 144 in the floor 142 and continues through the valve block 140 past a pressure-actuated one-way valve 146 and out through an outlet orifice 148 in the clamping surface 104. The valve 146 is set to open and thus allow the discharge of gas when the pressure inside the transport unit exceeds atmospheric pressure by a predetermined amount. When the transport unit 30 is docked to the door frame 24 the orifice 148 is positioned such that gas leaving the transport unit 30 enters the airlock compartment between the doors 94 and 110.

The gasket 114 of the transport door 110, ordinarily an airtight seal, will also act as a one-way valve allowing gas to discharge from the transport unit 30 if pressure inside the unit increases beyond a preset level. Gas discharged around the gasket 114 will also enter the airlock compartment when the transport unit is docked.

In order to discharge gas from the airlock compartment and to maintain a steady, elevated pressure inside the compartment, a second valve block 150 (FIG. 7) is provided below the floor 142 of the transport unit 30. Gas from the airlock compartment passes through an inlet orifice 152 in the clamping surface 104 and into the valve block 150, through a pressure activated one-way valve 154 and from there is discharged to the atmosphere through an outlet orifice 156.

To initially fill the chamber with the desired gas, the plastic hood 14 is folded gently around the shelves 20 to reduce the volume in the chamber while the chamber doors means 94 and/or valve 66 is open. Alternatively, the door means 94 may be closed and air is exhausted from the chamber by connecting a vacuum pump to the outlet means 64. The door 94 and the outlet valve 66 are then closed and the desired gas admitted to the chamber by opening one of the inlet valves 60, 61. When the chamber is filled, the inlet valve is closed; valve 66 is again opened; and gas is expelled from the chamber through the outlet means 64. The chamber may thus be filled and exhausted several times to assure that the final atmosphere inside the apparatus is as desired.

When the present invention is to be used as an anaerobic incubation means the chamber may be filled and vented several times with dry nitrogen and filled the final time with the gas mixture to be used during incubation. Anaerobic gases preferably include nitrogen, hydrogen and carbon dioxide in such a ratio that the mixture is not explosive if exposed to air and heat. The mixture of these gases may be varied to suit the particular cultures being incubated. One mixture, suitable for most anaerobic specimens, is 7 percent $H_2$, 5 percent $CO_2$ and 88 percent $N_2$.

If anaerobic conditions are to be maintained it is also convenient to provide an oxygen detection means, such as an indicator dye in the culture medium, to alert the operator if the atmosphere inside the chamber or transport unit becomes contaminated with oxygen.

Because oxygen will defuse from the surrounding atmosphere into the chamber 16 through the plastic hood 14 and gloves 18, it is necessary to replenish the gas inisde the chamber from time to time or to provide a means for removing oxygen from the gases inside the chamber. One suitable method of removing oxygen, provided that the gas mixture contains sufficient hydrogen, is to circulate the gas mixture through a bed of catalyst pellets which facilitate the reaction of oxygen with the hydrogen to form water. A preferred catalyst for this purpose is palladiumized alumina.

The catalyst pellets can conveniently be placed in catalyst trays 82 positioned over chamber inlet means 44 so that the blower 48 forces the heated gas in the plenum 42 through the catalyst pellets. Because the gas is heated the activity of the catalyst is increased. The efficiency of the catalyst decreases, however, as moisture builds up and also by poisoning with $H_2S$ given off by the anaerobes. The poisoning of catalyst pellets can be greatly reduced by placing a substance which reacts with hydrogen sulfide, such as a metal carbonate or sulfate, near the cultures. Silver sulfate is preferred for this use. Eventually, when the activity of the catalyst becomes low, it may be rejuvenated by heating in an oven at 100° C. for 2 hours. Multiple trays of catalysts may be used in the chamber 16 so that the catalyst can be rejuvenated one tray at a time. Additional catalyst pellets placed in the catalyst container 134 are useful to remove any trace amounts of oxygen present in the gas mixture which is introduced into the transport unit 30.

When a specimen at a remote location is to be transferred to the controlled atmosphere apparatus chamber the procedure is as follows. First, the specimen is placed inside the transport unit 30. The details of this step are illustrated in FIG. 8. The specimen is placed in a dish 160 containing culture media. A stream of a desired gas mixture is directed into the dish and a cover is then placed over it. The dish 160 is inserted into a cavity 162 of a filler block 164; and the block is placed inside the transport unit 30. The filler block 164 is designed to contain the glassware and to occupy essentially the entire interior volume of the transport unit 30 so as to minimize the volume of gas present in the transport unit and thus reduce the amount of air which must be flushed from inside the unit. A variety of different filler blocks may be provided to match different types of glassware, and as shown in FIG. 8, the filler block may consist of multiple layers which may be exchanged to produce a cavity 162 of any desired dimensions.

A desired gas mixture is admitted through the inlet 124 during the loading of the filler block 164 to expel air from the transport unit 30. Nitrogen or a mixture of nitrogen and other anaerobic gases are suitable for this purpose if the specimen consists of anaerobes. When the filler block is in position inside the transport unit 30, the door 110 is closed and an appropriate gas flow rate set according to the flow meter 126. The gas mixture continuously passes from the pressurized gas source and through the transport unit 30 until such time as the material can be transferred to the chamber 16. The gas mixture is automatically vented from the transport unit through the valve block 140 as previously described. Any excess pressure inside the transport unit 30 is relieved by gas flow around the gasket 114 of the door 110.

To transfer specimens from the transport unit 30 to the chamber 16, the transport unit 30 is docked as shown in FIG. 1 and secured by the clamps 34 to form the airlock compartment between the doors of the chamber and transport unit. After docking the flow rate of gas into the transport unit is reduced to an amount no greater than the maximum flow rate through the valve block 150. As previously described the valve block 150 vents the area between the doors 94 and 110 to the atmosphere. This flow is continued for about 5 minutes or as long as necessary to expel oxygen trapped in the airlock compartment. The valve 128 may then be closed to stop the flow. Next, the doors 94 and 110 are opened from the inside of the chamber 16, and the filler block 164 is transferred to the chamber without disturbing the atmosphere inside the chamber. The dish 160 is then removed from the filler block 164; and the block is replaced inside the transport unit 30.

The transport unit 30 is removed by closing both doors 94 and 110, unfastening the clamps 34 and removing the transport unit 30.

While we have shown and described a preferred embodiment of our invention, it will be apparent to those skilled in the art that changes and modifications may be made without departing from our invention in its broader aspects. We therefore intend the appended claims to cover all such changes and modifications as fall within the true spirit and scope of our invention.

We claim:

1. A controlled atmosphere system comprising:
    an apparatus having a base, a flexible hood joined to said base so that said hood and said base define an airtight chamber and a sealable chamber door means communicating with the atmosphere surrounding said chamber;
    a transport unit adapted to dock with said apparatus such that specimens may be transferred between the interior of said unit and said chamber without admitting gas from the surrounding atmosphere into said chamber, said transport unit including a sealable transport door means communicating with the atmosphere surrounding said transport unit, both said door means comprising swinging doors which are in opposition when both of said doors are closed and said transport unit is docked with said apparatus; and
    support means to maintain said transport unit at the level of said chamber door means when said transport unit is docked.

2. A controlled atmosphere system comprising:
    an apparatus having a base, a flexible hood joined to said base so that said hood and said base define an airtight chamber and a sealable chamber door means communicating with the atmosphere surrounding said chamber;
    a transport unit adapted to dock with said apparatus such that specimens may be transferred between the interior of said unit and said chamber without admitting gas from the surrounding atmosphere into said chamber, said transport unit including a sealable transport door means communicating with the atmosphere surrounding said transport unit, both said door means comprising swinging doors which are adapted to swing into said chamber to an open position when said transport unit is docked with said apparatus; and
    support means to maintain said transport unit at the level of said chamber door means when said transport unit is docked.

3. A controlled atmosphere system comprising:
    an apparatus having a base, a flexible hood joined to said base so that said hood and said base define an airtight chamber and a sealable chamber door means communicating with the atmosphere surrounding said chamber;
    a transport unit adapted to dock with said apparatus such that specimens may be transferred between the interior of said unit and said chamber without admitting gas from the surrounding atmosphere into said chamber, said transport unit including a sealable transport door means communicating with the atmosphere surrounding said transport unit;
    a gasket disposed between said apparatus and said transport unit to form an airtight seal when said transport unit is docked; and
    support means to maintain said transport unit at the level of said chamber door means when said transport unit is docked.

4. A controlled atmosphere system comprising:
    an apparatus having a base, a flexible hood joined to said base so that said hood and said base define an air-tight chamber and a sealable chamber door means communicating with the atmosphere surrounding said chamber;
    a transport unit adapted to dock with said apparatus such that specimens may be transferred between the interior of said unit and said chamber without admitting gas from the surrounding atmosphere into said chamber, said transport unit including a sealable transport door means communicating with the atmosphere surrounding said transport unit, said two door means being of sufficient size that a specimen container which occupies substantially the entire volume of the transport unit can pass through both of said door means; and support means to maintain said transport unit at the level of said chamber door means when said transport unit is docked.

5. A controlled atmosphere system comprising:

an apparatus having a base, a flexible hood joined to said base so that said hood and said base define an airtight chamber, a sealable chamber door means communicating with the atmosphere surrounding said chamber and a chamber door latch operable from the inside of said chamber to secure said chamber door means in a sealed position;

a transport unit adapted to dock with said apparatus such that specimens may be transferred between the interior of said unit and said chamber without admitting gas from the surrounding atmosphere into said chamber, said transport unit including a sealable transport door means communicating with the atmosphere surrounding said transport unit and a transport door latch which is both operable from the outside of said transport unit to secure said transport door means in a sealed position and accessible from the inside of said chamber when said chamber door means is open and said transport unit and said apparatus are docked together; and support means to maintain said transport unit at the level of said chamber door means when said transport unit is docked.

6. A controlled atmosphere system comprising:

an apparatus having a base, a flexible hood joined to said base so that said hood and said base define an airtight chamber, a sealable chamber door means communicating with the atmosphere surrounding said chamber and inlet and outlet means through which the gaseous medium flows into and out of said airtight chamber;

a transport unit adapted to dock with said apparatus such that specimens may be transferred between the interior of said unit and said chamber without admitting gas from the surrounding atmosphere into said chamber, said transport unit including a sealable transport door means communicating with the atmosphere surrounding said transport unit, inlet and outlet means and a flow meter for regulating the flow of gaseous medium through said transport unit and a gasket constructed such that when said transport door means is closed, gas in the surrounding atmosphere cannot flow past the gasket into said transport unit; and support means to maintain said transport unit at the level of said chamber door means when said transport unit is docked.

7. The system according to claim 6 constructed such that in airlock compartment is defined between said two door means when said transport unit is docked;

said transport unit outlet means exhausts gas from said transport unit into said airlock compartment; and further comprising one-way valve means for discharging gas from said airlock compartment.

8. The system according to claim 6 constructed so that gaseous medium in said chamber and transport unit are maintained at pressures above atmospheric and so that gaseous medium flows out around said gasket when the pressure in said transport unit exceed a desired level.

9. A hand held apparatus for transporting specimens from remote locations to an airtight incubation chamber and for maintaining specimens in a controlled atmosphere during transporting comprising:

a plurality of rigid walls which define a transport chamber for receiving a specimen to be transported between a remote location and an airtight incubation chamber;

a single door on one of said walls for admitting and discharging specimens;

docking means adapted for detachably joining said apparatus with said incubation chamber such that specimens may be transferred between said incubation and transport chambers without admitting gas from the surrounding atmosphere into either of said chambers;

means for circulating a selected gaseous medium through said transport chamber to displace any residual gas therein and to establish a selected atmosphere therein including an inlet valve for introducing said selected gaseous medium into said transport chamber and an outlet valve for simultaneously exhausting said gaseous medium from said transport chamber, one of said valves being mounted on and comprising an integral part of said hand held apparatus;

said inlet valve and said outlet valve being disposed such that selected gaseous medium introduced through said inlet valve flows through said transport chamber from one end thereof to the other, from said inlet valve to said outlet valve.

10. A method of transferring oxygen-sensitive specimens from a remote location to an incubator apparatus having an anaerobic atmosphere comprising:

placing the specimens in an airtight transport chamber;

transporting the chamber to an incubator apparatus;

circulating an anaerobic gaseous medium through the chamber at greater than atmospheric pressure during said transporting;

docking the chamber with the apparatus to form an airlock between said chamber and apparatus; and transferring specimens from said chamber, through said airlock and into said apparatus.

11. The method according to claim 10 further comprising:

flushing the specimens with a stream of anaerobic gas; and placing said specimens in a filler block prior to said placing of the specimens in the transport chamber.

12. A controlled atmosphere system comprising:

an apparatus having walls which define an airtight chamber, one of said walls having an opening therethrough and sealing chamber door means mounted thereon to close said opening;

a transport unit having airtight walls which define an interior zone for receiving an atmosphere-sensitive article to be transported between a remote location and said apparatus, one of said transport unit walls having an opening therethrough and a sealing transport unit door means mounted thereon to close said transport unit wall opening, said transport unit being adapted to dock detachably with said apparatus to form an airlock compartment therebetween so that articles may be transferred between said zone and said chamber through said openings without admitting gas from the surrounding atmosphere;

means for circulating a selected gaseous medium through said zone to displace any residual gas therein and to establish a selected atmosphere therein including inlet means for introducing said selected gaseous medium into said zone and outlet means adapted for simultaneously exhausting gaseous medium from said zone; and means for circulating a selected gaseous medium through said airlock compartment wherein said outlet means is positioned such that gaseous medium exhausted from said zone passes into said compartment when said transport unit is docked and said transport unit door means is closed and including means for exhausting said gaseous medium from said compartment to the surrounding atmosphere so that any residual air trapped in said compartment as a result of docking can be displaced, through said means for exhausting, simultaneously with the admission of said selected gaseous medium into said compartment via said outlet means, prior to the transfer of an atmosphere-sensitive article between said chamber and said zone.

13. The system of claim 12 wherein said means for exhausting comprises a one-way valve.

14. The system of claim 12 wherein said inlet means comprises a one-way valve.

15. The system of claim 12 wherein said outlet means comprises a one-way valve.

16. The system of claim 12 wherein said outlet means comprises a gasket between said transport unit door means and said one of said transport unit walls, said gasket being constructed such that when said transport unit door means is closed, gas outside of said zone can not flow past said gasket into said zone, but gas in said zone will flow past said gasket into the surrounding atmosphere if pressure inside said zone is substantially above the pressure of said surrounding atmosphere.

17. The system of claim 12 further comprising flow meter means for regulating the flow of said gaseous medium through said inlet means.

18. A method of transferring an atmosphere-sensitive article from a remote location to a controlled atmosphere apparatus having an airtight chamber filled with a special gaseous medium comprising:

enclosing an atmosphere-sensitive article in an interior zone of an airtight transport unit;

circulating a special gaseous medium through said zone to displace any residual air located therein;

transporting the transport unit, containing said article and a volume of said special gaseous medium, to a controlled atmosphere apparatus;

docking said transport unit with said apparatus to form an airlock compartment therebetween;

circulating a special gaseous medium into said zone, from said zone into said compartment and from said compartment into the surrounding atmosphere to displace any residual air trapped in said compartment as a result of said docking; and transferring said articles from said zone through said compartment and into said apparatus.

19. The method of claim 18 wherein said special gaseous media comprise anaerobic gases.

* * * * *